US011609537B2

(12) United States Patent
Kondo et al.

(10) Patent No.: US 11,609,537 B2
(45) Date of Patent: Mar. 21, 2023

(54) CELL ANALYSIS METHOD AND CELL ANALYSIS SYSTEM USING A HOLOGRAPHIC MICROSCOPE (71) Applicants: SHIMADZU CORPORATION, Kyoto (JP); iPS PORTAL, Inc., Kyoto (JP)

(72) Inventors: Yasushi Kondo, Kyoto (JP); Shuhei Yamamoto, Kyoto (JP); Mika Okada, Kyoto (JP); Minoru Okada, Hirakata (JP)

(73) Assignees: SHIMADZU CORPORATION, Kyoto (JP); iPS PORTAL, Inc., Kyoto (JP)

( * ) Notice: Subject to any disclaimer, the term of this patent is extended or adjusted under 35 U.S.C. 154(b) by 753 days.

(21) Appl. No.: 16/490,123

(22) PCT Filed: Mar. 2, 2017

(86) PCT No.: PCT/JP2017/008230
§ 371 (c)(1),
(2) Date: Oct. 30, 2019

(87) PCT Pub. No.: WO2018/158901
PCT Pub. Date: Sep. 7, 2018

(65) Prior Publication Data
US 2020/0057294 A1 Feb. 20, 2020

(51) Int. Cl.
G03H 1/04 (2006.01)
C12M 1/34 (2006.01)
(Continued)

(52) U.S. Cl.
CPC .......... G03H 1/0443 (2013.01); C12M 41/46 (2013.01); G01N 15/0227 (2013.01);
(Continued)

(58) Field of Classification Search
CPC ............... G01N 33/50; G01N 33/5073; G01N 15/0227; G01N 2015/0065;
(Continued)

(56) References Cited

U.S. PATENT DOCUMENTS

2011/0157601 A1 6/2011 Sebesta et al.
2012/0315620 A1 12/2012 Watakabe et al.
(Continued)

FOREIGN PATENT DOCUMENTS

EP 2300880 3/2011
EP 2487249 A1 8/2012
(Continued)

OTHER PUBLICATIONS

International Search Report of PCT/JP2017/008230 dated May 30, 2017 [PCT/ISA/210].
(Continued)

Primary Examiner — Michael P LaPage
(74) Attorney, Agent, or Firm — Sughrue Mion, PLLC (57) ABSTRACT A cell area extraction unit (241) extracts a cell area in a phase image that is created based on a hologram obtained by in-line holographic microscope (IHM). A background value acquisition unit (242) obtains a background value from phase values at a plurality of positions outside the cell area. An intracellular phase value acquisition unit (243) averages a plurality of phase values on a sampling line set at a position close to the periphery of a cell, while avoiding a central portion in which the phase value may be lowered in the cell area, to obtain an intracellular phase value. A phase change amount calculation unit (244) obtains the difference between the intracellular phase value and the background value. A phase change amount determination unit (245) compares the value of the difference with thresholds in two levels to determine whether the cell is in an undifferentiated state or (Continued)

an undifferentiation deviant state. It is thereby possible to automatically make a correct determination while removing the influence of a theoretical measurement error by IHM.

10 Claims, 5 Drawing Sheets (51) Int. Cl.
G02B 21/36 (2006.01)
G03H 1/08 (2006.01)
G01N 15/02 (2006.01)
G02B 21/00 (2006.01)
G03H 1/00 (2006.01)
G01N 15/00 (2006.01)

(52) U.S. Cl.
CPC ......... *G02B 21/0056* (2013.01); *G02B 21/36* (2013.01); *G03H 1/0866* (2013.01); *G01N 2015/0065* (2013.01); *G01N 2015/0233* (2013.01); *G03H 2001/005* (2013.01)

(58) Field of Classification Search
CPC ....... G01N 2015/0233; G01N 15/1434; G01N 15/1468; G01N 2015/1006; G01N 2015/1454; G02B 21/36; G02B 21/0032; G02B 21/0056; G02B 21/008; C12M 41/46; C12M 41/36; G03H 1/0443; G03H 1/0866; G03H 2001/005; G03H 2001/0447
See application file for complete search history.

(56) References Cited

U.S. PATENT DOCUMENTS

| 2014/0307079 | A1 | 10/2014 | Aragaki | |
| 2016/0160170 | A1* | 6/2016 | Matsubara | G02B 21/14 435/287.1 |
| 2016/0349170 | A1* | 12/2016 | Nakatsuji | G06V 20/698 |
| 2016/0370569 | A1 | 12/2016 | Matsumoto | |
| 2017/0132450 | A1* | 5/2017 | El-Zehiry | G06T 7/136 |
| 2017/0199171 | A1* | 7/2017 | Kiyota | G06V 20/698 |
| 2017/0212033 | A1* | 7/2017 | Ozaki | G01B 11/06 |
| 2017/0270388 | A1* | 9/2017 | Vercruysse | G06K 9/6267 |
| 2017/0329281 | A1 | 11/2017 | Tagawa | |

FOREIGN PATENT DOCUMENTS

| JP | 10-268740 A | 10/1998 |
| JP | 3471556 B2 | 12/2003 |
| JP | 2011-525252 A | 9/2011 |
| JP | 2013-158325 A | 8/2013 |
| JP | 2014-018184 A | 2/2014 |
| JP | 2015-165785 A | 9/2015 |
| WO | 2009154558 A1 | 12/2009 |
| WO | 2011/043077 A1 | 4/2011 |
| WO | 2013/099772 A1 | 7/2013 |
| WO | 2014017480 A1 | 1/2014 |
| WO | 2014/203322 A1 | 12/2014 |
| WO | 2015/076311 A1 | 5/2015 |
| WO | 2015133185 A1 | 9/2015 |
| WO | 2016/084420 A1 | 6/2016 |

OTHER PUBLICATIONS

Written Opinion of PCT/JP2017/008230 dated May 30, 2017 [PCT/ISA/237].
Barer, R., "Interference Microscopy and Mass Determination", Nature, vol. 169, Mar. 1, 1952, pp. 366-367.
Awatsuji, Y., "Development of technique and system for three-dimensional measurement of moving cells by means of parallel digital holographic microscopy", Feature Article, Readout, Horiba Ltd., Dec. 2009, No. 35, pp. 10-15.
Stahl, R., et al., "Lens-free digital in-line holographic imaging for wide field-of-view, high resolution and real-time monitoring of complex microscopic objects", Proc. of SPIE, vol. 8947, pp. 1-10.
Office Action dated Jun. 7, 2022 issued the by Chinese Patent Office in Chinese Application No. 201780087860.5.

* cited by examiner

Fig. 8A AFTER 2 DAYS

Fig. 8B AFTER 4 DAYS

Fig. 8C AFTER 6 DAYS

CELL ANALYSIS METHOD AND CELL ANALYSIS SYSTEM USING A HOLOGRAPHIC MICROSCOPE

TECHNICAL FIELD

The present invention relates to a cell analysis method and a cell analysis system for noninvasively analyzing the state of a cell in the process of culturing pluripotent stem cells (embryonic stem (ES) cells and induced pluripotent stem (iPS) cells), or the like. More specifically, the present invention relates to a cell analysis method and a cell analysis system for analyzing a cell based on a phase image of an object, calculated from a hologram obtained by a digital holography device recording interference pattern between an object wave and a reference wave.

BACKGROUND ART

In the field of regenerative medicine, in recent years, studies using pluripotent stem cells such as iPS cells and ES cells have been conducted actively. A cell is generally transparent and difficult to observe with a normal optical microscope, and hence a phase-contrast microscope has been widely used for observing a cell. However, in the phase-contrast microscope, focusing is required at the time of taking a microscopic image, thus causing a problem where measurement takes time. For solving this, a holographic microscope using digital holography technology has recently been developed and put to practical use (cf. Patent Literature 1 etc.).

The holographic microscope acquires an interference pattern (hologram) formed on the detection surface of an image sensor or the like by object light which is light from a light source reflected or transmitted on the surface of an object and reference light directly reaching from the same light source, and performs predetermined arithmetic processing based on the hologram to obtain an intensity image or a phase image as a reconstructed image of the object. Such a holographic microscope can perform focusing at the data processing stage after acquiring a hologram, that is, can form a reconstructed image in focus, thereby eliminating the need to perform focusing for each photographing and has an advantage of shortening the measurement time.

Meanwhile, in research and development of regenerative medicine using pluripotent stem cells, it is necessary to culture a large number of undifferentiated cells in a state where pluripotency is maintained. Therefore, it is necessary to select an appropriate culture environment and stably control the environment, and also to frequently check the state of cells in culture. For example, when a cell in a cell colony deviates from the undifferentiated state, all cells in the cell colony finally shift to an undifferentiation deviant state, because all cells in the colony have an ability to differentiate. For this reason, an observer needs to check daily for any occurrence of a cell deviated from the undifferentiated state (a cell having already been differentiated or a cell likely to be differentiated, hereinafter referred to as an "undifferentiation deviant cell") among the cells in culture. When an undifferentiation deviant cell is found, the cell needs to be removed quickly.

It is possible to reliably determine whether or not pluripotent stem cells are kept in the undifferentiated state by staining the cells with undifferentiation markers. However, since the stained cells die, undifferentiation marker staining cannot be performed to determine the pluripotent stem cells for regenerative medicine. Therefore, at the present field of the cell culture for regenerative medicine, the observer determines whether or not the cell is an undifferentiated cell based on the morphological observation of the cell by using the phase-contrast microscope described above. However, making a correct identification in such a method requires a skill. In addition, the determination inevitably varies since being made based on human judgment. Therefore, such a conventional technique is not suitable for industrial mass production of pluripotent stein cells.

CITATION LIST

Patent Literature

Patent Literature 1: WO 2016/084420 A
Patent Literature 2: JP H10-268740 A
Patent Literature 3: WO 2013/099772 A

Non Patent Literature

Non Patent Literature 1: "Interference Microscopy and Mass Determination", written by Barer, Nature, 1952, Vol. 169, pp. 366-367

SUMMARY OF INVENTION

Technical Problem

The present invention has been made to solve the above problems, and an object of the present invention is to provide a cell analysis method and a cell analysis system capable of correctly and efficiently determining whether a pluripotent stem cell such as an iPS cell or an ES cell is in an undifferentiated state or an undifferentiation deviant cell by using a noninvasive cell observation method.

Solution to Problem

In the past research (cf. Non Patent Literature 1), it has been reported that a change in phase obtained in observation using a phase-contrast microscope, a differential interference microscope, or the like may be proportional to the total amount of dry matter of protein contained in the cell to be observed. According to such a finding, it is presumed that by comparing the amount of change in phase on a cell basis or cell colony basis, the state of a cell can be compared, and the discrimination between the cell in the undifferentiated state and the cell in the undifferentiation deviant state is possible. The present inventors have repeated experiments focusing on this point and reached the completion of the present invention.

The cell analysis method according to the present invention is a cell analysis method using a holographic microscope, the method including:

a) a cell area extraction step of extracting a cell area in which a cell to be analyzed is present in a phase image of an area including the cell area, the phase image being obtained from a hologram with a holographic microscope;

b) a background value acquisition step of calculating a background value based on phase values at a plurality of positions in the area excluding the cell area in the phase image;

c) an intracellular phase value acquisition step of obtaining an intracellular phase value based on phase values at a plurality of positions in a measurement target range between a contour line of the cell in the cell area and a virtual line spaced a predetermined distance inward from the contour line; and d) a cell state determination step of determining whether the cell to be analyzed is in an undifferentiated state or an undifferentiation deviant state based on a difference between the phase value obtained in the intracellular phase value acquisition step and the background value.

The cell analysis system according to the present invention which has been made to solve the above problem is a system for carrying out the cell analysis method according to the present invention and is a cell analysis system using a holographic microscope, the system including:

a) a cell area extraction unit that extracts a cell area in which a cell to be analyzed is present in a phase image of an area including the cell area, the phase image being obtained from a hologram with a holographic microscope;

b) a background value acquisition unit that calculates a background value based on phase values at a plurality of positions in the area excluding the cell area in the phase image;

c) an intracellular phase value acquisition unit that obtains an intracellular phase value based on phase values at a plurality of positions in a measurement target range between a contour line of the cell in the cell area and a virtual line spaced a predetermined distance inward from the contour line; and d) a cell state determination unit that determines whether the cell to be analyzed is in an undifferentiated state or an undifferentiation deviant state based on a difference between the phase value obtained by the intracellular phase value acquisition unit and the background value.

In the cell analysis method and the cell analysis system according to the present invention, the cell to be analyzed is typically a pluripotent stem cell such as an iPS cell or an ES cell.

In the cell analysis system according to the present invention, in the holographic microscope, for example, a hologram of an area including a cell to be analyzed, which is being cultured in a culture plate, is acquired. By performing predetermined data processing (phase recovery and image reconstruction) on the acquired hologram data, a phase image of the area including the cell to be analyzed is created. A series of processing up to this phase image creation is performed with a conventional general holographic microscope.

In the cell analysis system according to the present invention, the cell area extraction unit performs processing according to a predetermined algorithm on the phase image to extract a cell area in which a cell to be analyzed is present. For the extraction of the cell area, a known method such as texture analysis frequently used in the field of image recognition may be used. By extracting the cell area, the phase image is divided into the cell area and a non-cell area in which no cell to be analyzed is present. Therefore, the background value acquisition unit acquires phase values at a plurality of positions in the non-cell area, and calculates a background value by, for example, averaging the plurality of phase values. Even in the non-cell area, there are cases where the phase value is slightly higher than the others due to waste or a dead cell contained in a culture medium or a hologram generated caused by a scratch on the culture plate, or the like. Therefore, it is desirable to avoid using an apparently abnormal phase value in the calculation of the background value by an appropriate pre-processing, such as selecting a range in which the phase value is a predetermined threshold or smaller in the non-cell area.

On the other hand, the intracellular phase value acquisition unit calculates the representative value of the phase value in the cell area, that is, the intracellular phase value, based on phase values at a plurality of positions in the cell area. When the variation in the phase value in the cell area is small, the intracellular phase value may be determined using phase values at a plurality of arbitrarily determined positions in the cell area. However, it has been found that, when an in-line holographic microscope is used as the holographic microscope, in which a hologram is created from object light flux and reference light flux running close to each other, a theoretical measurement error occurs due to the disturbance of the reference light if the size of the cell being observed is large. This measurement error becomes larger as the position is farther from the periphery of the cell, that is, as the position is closer to the center of the cell, and the measurement error is observed as a decrease in the phase value. Therefore, there is no problem when the cell is small, but when the cell is large, although a correct phase value, that is, a phase value reflecting the actual optical thickness, is obtained at a position close to the cell periphery, a small phase value not reflecting the actual optical thickness may be obtained at a position close to the center. Therefore, in order to avoid the use of such an incorrect phase value, the intracellular phase value acquisition unit calculates an intracellular phase value based on phase values at a plurality of positions within a measurement target range between a contour line of the cell in the cell area (the boundary between the cell area and the non-cell area) and a virtual line spaced a predetermined distance inward from the contour line, that is, a portion close to the periphery of the cell.

In the case of pluripotent stem cells, the decrease in phase value as described above occurs in the case of a cell colony in which a large number of cells are collected, and such a problem does not occur in a small single cell. That is, in a single cell, a phase value at any position in the cell area can be used to calculate an intracellular phase value.

Therefore, in the cell analysis method and the cell analysis system according to the present invention, the predetermined distance may be a value set in advance so that the whole cell is included in the measurement target range when the cell to be analyzed is a single cell.

If the predetermined distance is made excessively large, there is a possibility, of course, that a portion showing an incorrect phase value in a large cell may fall within the measurement target range.

Therefore, in the cell analysis method and the cell analysis system according to the present invention, when the holographic microscope is an in-line holographic microscope, the measurement target range is preferably determined as the range in the cell area indicating a relatively high phase value compared to an area that is surrounded by the measurement target range.

When a decrease in phase value is observed at the position close to the center of the cell even though the optical thickness of cell is almost constant, there is a tendency that the phase value is almost constant in the range of a certain distance inward from the contour line of the cell, and then the phase value gradually decreases as the position goes inward. In the study through experiments by the present inventors, it is presumed that, the position where the phase value begins to decrease from the almost constant state in the cell area depends on the size of the cell, but the phase value in the portion close to the cell periphery is almost stable. Therefore, the measurement target range which is not affected by the decrease in phase value, that is, the distance, can be appropriately set in advance by experiment or the like. Specifically, in the study of the present inventors, a favorable determination can be made when the distance is set to about more than 10 to 20 μm at the time of observing the iPS cell.

When the intracellular phase value is obtained by the intracellular phase value acquisition unit, as described above, the cell state determination unit calculates the difference between the intracellular phase value and the background value. Then the cell state determination unit determines whether the cell to be analyzed is in the undifferentiated state or the undifferentiation deviant state by, for example, comparing the difference with a predetermined threshold. By subtracting the background value from the intracellular phase value, environmental factors such as the fluctuation in the brightness of the light source of the holographic microscope are excluded to obtain a highly accurate phase value corresponding to the cell to be analyzed. Further, since there is a significant difference in phase value between the cell in the undifferentiated state and the undifferentiation deviant cell, the cell state determination unit can determine with high accuracy whether the cell is in the undifferentiated state or the undifferentiation deviant state.

However, in practice, it is difficult to determine whether the cell is in the undifferentiated state or the undifferentiation deviant state with a single threshold value. Further, in the field of cell culture for regenerative medicine, it is desirable to make the determination error as close to zero as possible.

Therefore, in the cell analysis system according to the present invention, the cell state determination unit may preferably judge that the cell to be analyzed is in the undifferentiation deviant state when the difference is equal to or greater than a first threshold value, and judge that the cell to be analyzed is in the undifferentiated state when the difference is equal to or smaller than a second threshold value that is smaller than the first threshold value.

As one aspect of the cell analysis system according to the present invention, the intracellular phase value acquisition unit may set a sampling line along a contour line of the cell within the measurement target range, calculate an average value of a plurality of phase values obtained on the sampling line, and take the average value as the intracellular phase value.

Advantageous Effects of Invention

According to the cell analysis method and cell analysis system according to the present invention, for example, in the field where pluripotent stem cells such as iPS cells and ES cells are cultured, it is possible to determine mechanically, that is, automatically correctly, whether the cell in culture maintains the undifferentiated state or is in the undifferentiation deviant state, without depending on the judgment of the observer. Hence variations in determination due to the proficiency and the skill of the observer are eliminated, and a quick determination can be made. This can result in the facilitation of the quality control of cells in culture and improvement in productivity.

BRIEF DESCRIPTION OF DRAWINGS

FIGS. 5A and 5B are schematic views showing a setting example of a line for the cell colony determination, where FIG. 5A is in the case of a cell colony, and FIG. 5B is in the case of a single cell.

FIGS. 6A and 6B are schematic views showing a setting example of a sampling line for calculating an intracellular phase value, where FIG. 6A is the case of the cell colony, and FIG. 6B is the case of the single cell.

FIGS. 7A and 7B are schematic views showing the schematic relationship between the position in the cross-sectional direction in the cell and the phase value, where FIG. 7A is the case of the cell colony, and FIG. 7B is the case of the single cell.

DESCRIPTION OF EMBODIMENTS

Hereinafter, an embodiment of a cell analysis system according to the present invention will be described with reference to the attached drawings.

Figure 1:
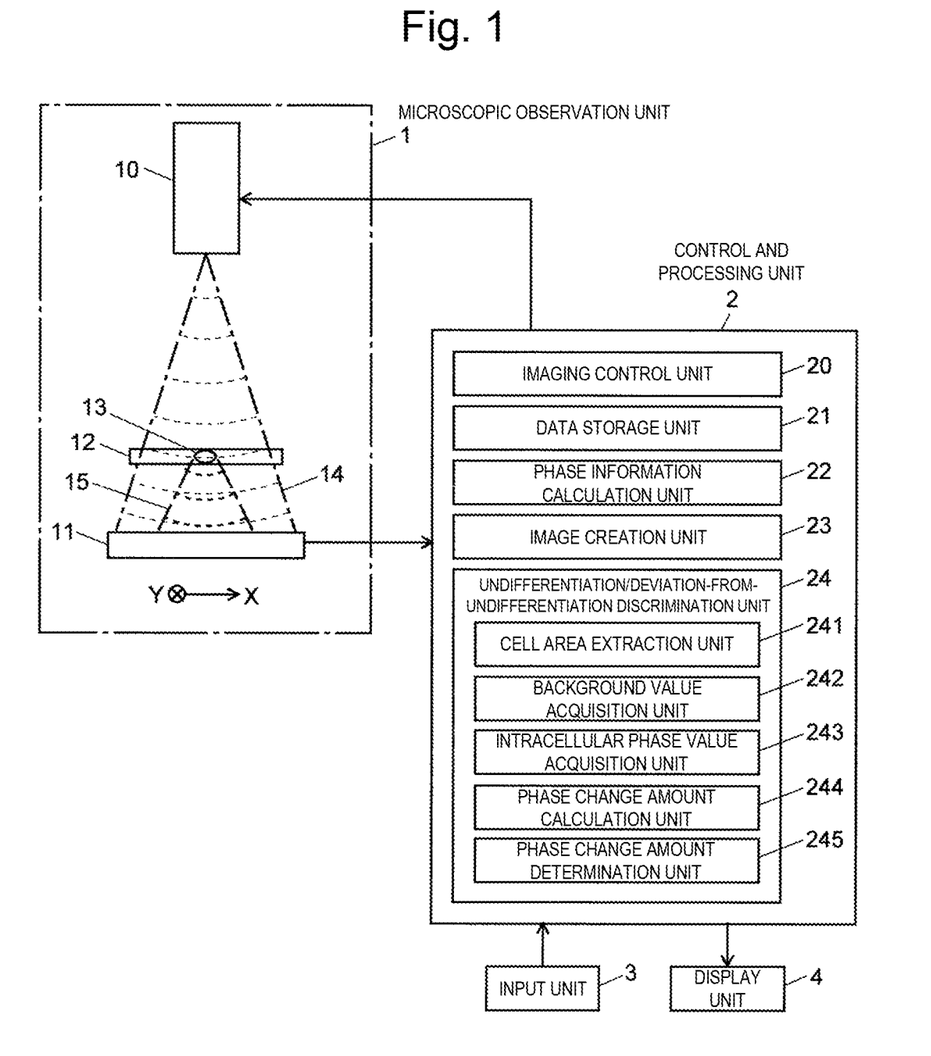
FIG. 1 is a schematic configuration diagram of a cell analysis system according to an embodiment of the present invention.

FIG. 1 is a schematic configuration diagram of a cell analysis system according to the present embodiment.

The cell analysis system of the present embodiment includes a microscopic observation unit 1, a control and processing unit 2, an input unit 3 which is a user interface, and a display unit 4.

The microscopic observation unit 1 is a microscope for in-line holographic microscopy (IHM) and includes a light source unit 10 including a laser diode and the like and an image sensor 11. A culture plate (or another cell culture vessel) 12 containing a cell 13 to be observed is arranged between the light source unit 10 and the image sensor 11. The control and processing unit 2 controls the operation of the microscopic observation unit 1 and processes the data acquired in the microscopic observation unit 1. The control and processing unit 2 includes, as function blocks, an imaging control unit 20, a data storage unit 21, a phase information calculation unit 22, an image creation unit 23, and an undifferentiation/deviation-from-undifferentiation discrimination unit 24. In addition, the undifferentiation/deviation-from-undifferentiation discrimination unit 24 includes, as lower function blocks, a cell area extraction unit 241, a background value acquisition unit 242, an intracellular phase value acquisition unit 243, a phase change amount calculation unit 244, and a phase change amount determination unit 245.

The substance of the control and processing unit 2 is a personal computer or a higher-performance workstation, and the function of each of the above functional blocks can be realized by operating, on the computer, dedicated control and processing software installed on the computer. Further, as described later, the functions of the control and processing unit 2 can be shared by a plurality of computers connected via a communication network, instead of being performed by one computer.

In the cell analysis system of the present embodiment, when a user (operator) sets a culture plate 12 containing the cell (a pluripotent stem cell 13 to be analyzed at a predetermined position and performs a predetermined operation in the input unit 3, the imaging control unit 20 controls the microscopic observation unit 1 so as to acquire data as follows.

That is, the light source unit 10 irradiates a predetermined area of the culture plate 12 with coherent light having a spread at a minute angle of about 10°. The coherent light (object light 15) transmitted through the culture plate 12 and the cell 13 reaches the image sensor 11 while interfering with light (reference light 14) transmitted through the area close to the cell 13 on the culture plate 12. The object light 15 is light with its phase changed at the time of transmission through the cell 13, while the reference light 14 is light that is not transmitted through the cell 13 and is thus not subjected to the phase change due to the cell 13. Therefore, on the detection surface (image surface) of the image sensor 11, an interference image (hologram) between the object light 15 with its phase changed by the cell 13 and the reference light 14 with its phase unchanged is formed.

The culture plate 12 is sequentially moved in the X-axis to Y-axis direction (in the plane perpendicular to the paper surface of FIG. 1) by a moving mechanism (not shown). Thereby, the irradiation area (observation area) of the coherent light emitted from the light source unit 10 can be moved on the culture plate 12, and a hologram can be acquired over a wide two-dimensional area.

As described above, the hologram data (two-dimensional light intensity distribution data of the hologram formed on the detection surface of the image sensor 11) obtained by the microscopic observation unit 1 is sequentially sent to the control and processing unit 2 and stored into the data storage unit 21. In the control and processing unit 2, the phase information calculation unit 22 reads the hologram data from the data storage unit 21 and executes predetermined arithmetic processing to calculate phase information of the entire observation area. Then, the image creation unit 23 creates a phase image of the entire observation area based on the calculated phase information. At the time of calculating the phase information or creating the phase image as thus described, a known algorithm disclosed in Patent Literatures 1 and 2 may be used. Note that intensity information, pseudo phase information, and the like may also be calculated based on the hologram data, and a reconstructed image based on these may be created. However, here, at least a phase image can be obtained, and the creation of other reconstructed images is not essential.

Figure 2:
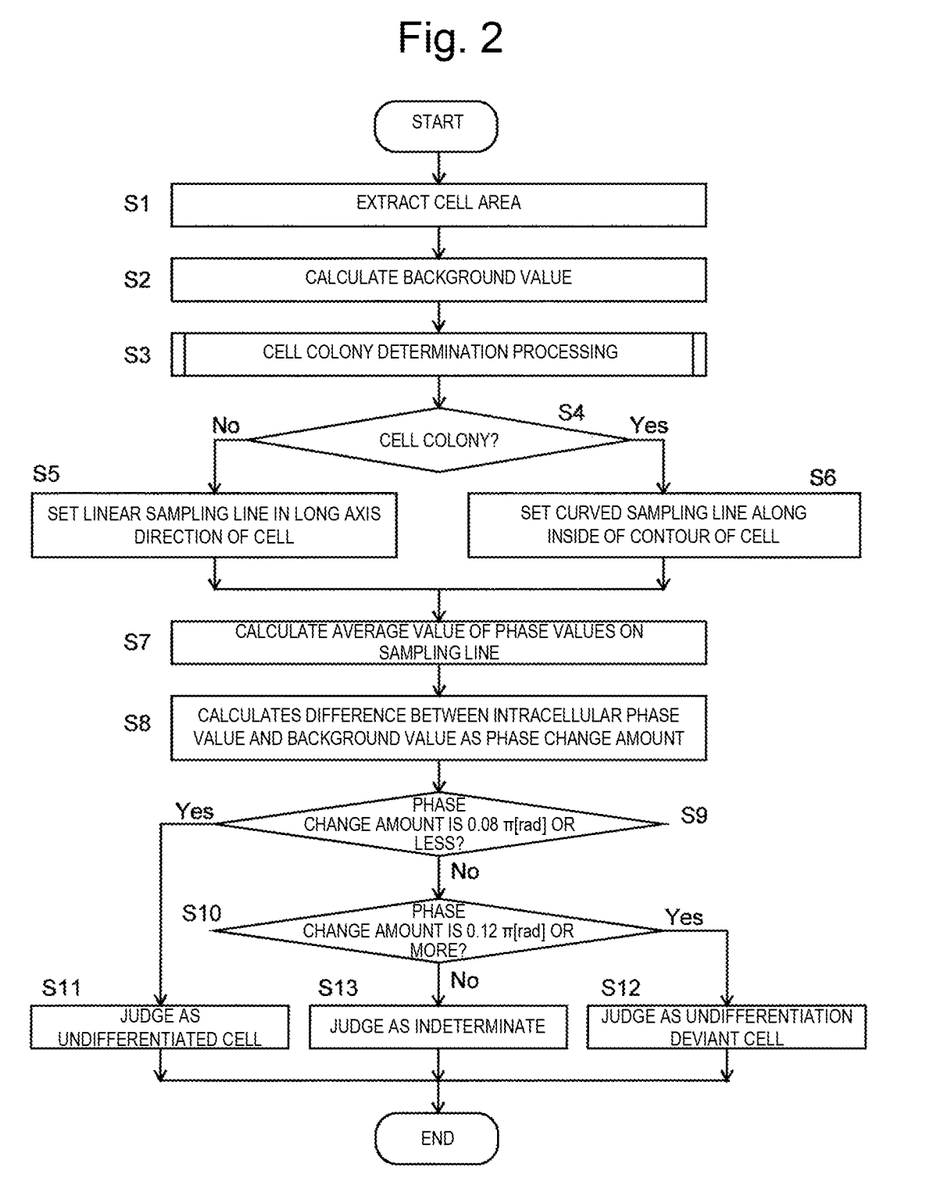
FIG. 2 is a flowchart showing the procedure of cell determination processing in the cell analysis system of the present embodiment.
Figure 3:
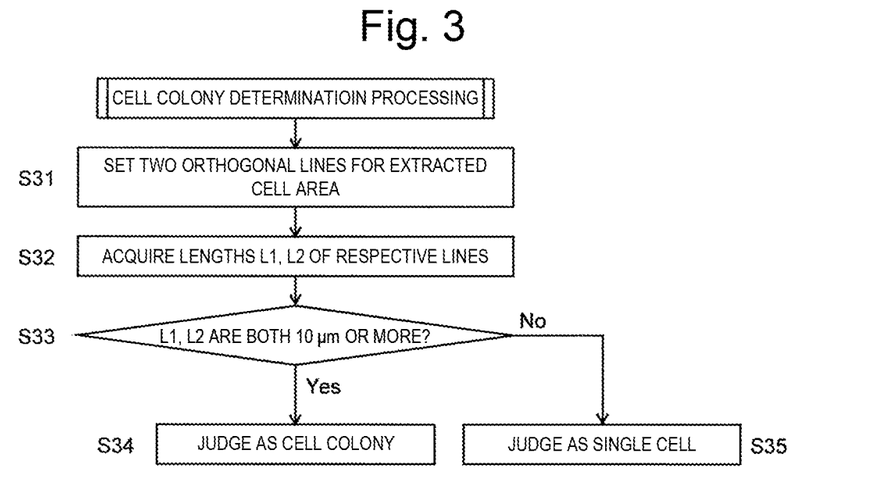
FIG. 3 is a detailed flowchart of cell colony determination processing in FIG. 2.

When the phase image in which the cell 13 to be observed is reflected as an image is obtained as described above, the undifferentiation/deviation-from-undifferentiation discrimination unit 24 executes discrimination processing in the procedure shown in FIG. 2. FIG. 2 is a flowchart showing the procedure of cell determination processing in the cell analysis system of the present embodiment, and FIG. 3 is a detailed flowchart of cell colony determination processing in FIG. 2.

First, the cell area extraction unit 241 extracts a cell area in which a cell or a cell colony is presumed to be present in the phase image based on the data forming the phase image and obtains data indicating the contour of the cell area (step S1). Although there may be one cell area, there are usually a plurality of cell areas. For extracting the cell area, it is possible to use a known algorithm widely used for image matching, such as texture image extraction or an image processing algorithm that determines luminance values against a threshold (cf. Patent Literature 3 etc.).

Next, in an area excluding the extracted cell area in the phase image, the background value acquisition unit 242 sets an area having a phase value close to 0 [rad], specifically, an area in which the absolute value of the phase value is smaller than a preset value, as a background area (non-cell area) and sets a predetermined number (e.g., five) of sampling lines with a predetermined length (e.g., 100 μm) in the background area. Then, the phase values at the respective positions on the plurality of sampling lines are determined, and the average value of all the phase values is calculated. Then, the calculation result is set as the background value in this phase image (step S2).

On the other hand, the intracellular phase value acquisition unit 243 determines, for each of the cell areas extracted in step S1, whether the cell area is a single cell or a cell colony in which a plurality of cells are collected (step S3).

Specifically, as shown in FIG. 3, first, for each cell area, two lines are set, one straight line having the largest length in the cell area portion among arbitrary straight lines crossing the cell area, and the other straight line having the largest length in the cell area portion among straight lines orthogonal to the one straight line (step S31).

Figure 4A:
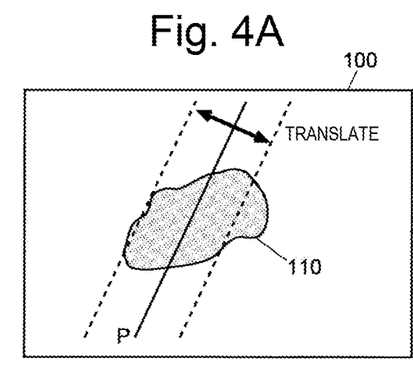
FIGS. 4A and 4B are schematic views for explaining a line setting method for cell colony determination.
Figure 4B:
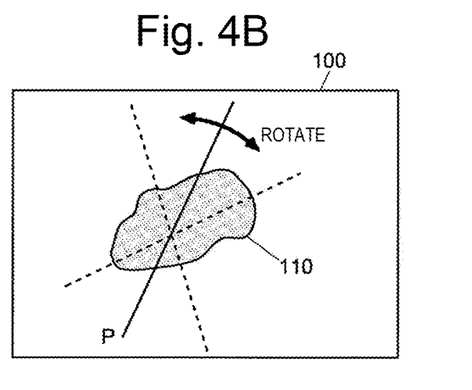

The position of the first straight line may be set by finding the position where the length of a cell area 110 portion is maximum, while combining the processing of translating a straight line P across the cell area 110 in a phase image 100 as shown in FIG. 4A and the processing of rotating the straight line P across the cell area 110 in the phase image 100 as shown in FIG. 4B. Once the position of the first straight line is determined, the position of the second straight line can be determined by examining the length of the cell area 110 portion while translating a straight line orthogonal to the straight line.

Figure 5A:
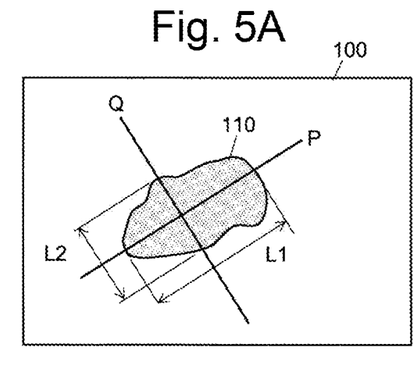
Figure 5B:
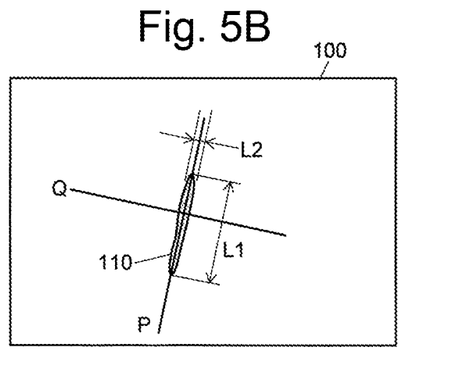

FIGS. 5A and 5B are a schematic view showing a state in which two lines are set on the cell area 110 in the phase image 100. Generally, a pluripotent stem cell has an elongated shape as shown in FIG. 5B, while a cell colony is a collection of many single cells and are thus near-circular and large compared to the single cell as shown in FIG. 5A. Therefore, here, it is determined whether the cell area is a single cell or a cell colony based on the lengths of the cell area portion for two lines P and Q set on the cell area 110.

That is, as shown in FIGS. 5A and 5B, the lengths L1 and L2 of the cell area 110 portion are obtained for the two lines P and Q (step S32), and it is determined whether or not both the lengths L1 and L2 are a predetermined length (here, 10 μm) or more (step S33). When both lengths are the predetermined length or more, it is judged that the cell area is a cell colony (step S34), and when at least either length is less than the predetermined length, it is judged that the cell area is a single cell (step S35). For example, in the example of the single cell shown in FIG. 5B, even when the length L1 is 10 min or more, the length L2 cannot normally be 10 μm or more, so that the cell area can be correctly judged as a single cell.

Figure 6A:
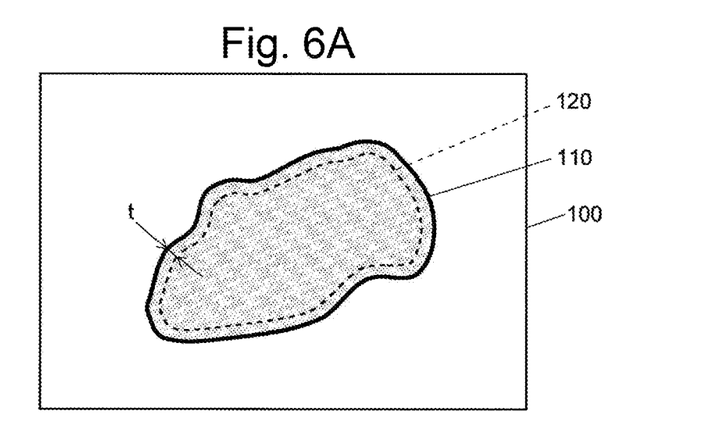
Figure 6B:
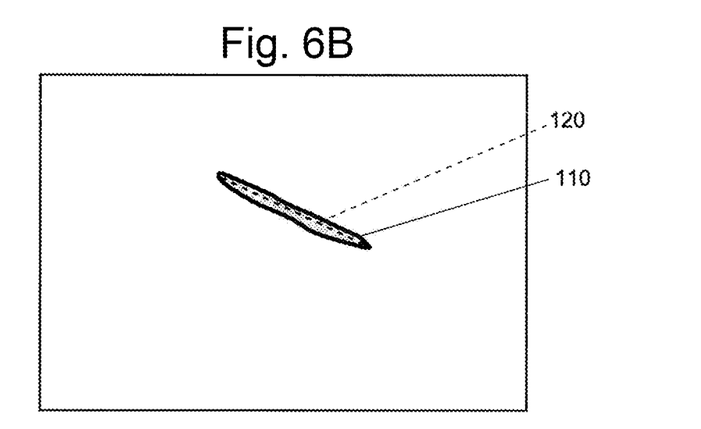

When the judgment in step S34 is made, the result in step S4 is Yes. In this case, a portion with an extremely large phase value is present around the contour line of the cell area 110 having a shape close to a circle in the phase image 100. Therefore, the intracellular phase value acquisition unit 243 finds, for example, a portion where the phase value is a predetermined threshold (here, 0.95 π[rad]) or more and sets a curved sampling line 120 along a contour line, which is inside the portion, at a position spaced inwardly from the contour line by a predetermined distance t, as shown in FIG. 6A (step S6). On the other hand, when the judgment of step S35 is made, the result in step S4 is No. In this case, as shown in FIG. 6B, the intracellular phase value acquisition unit 243 sets a linear sampling line 120 in the long axis direction of the elongated cell area 110 in the phase image 100 (step S5). An appropriate predetermined distance t is typically about 10 mm, and the reason for this will be described later.

When the sampling line 120 is determined, the intracellular phase value acquisition unit 243 obtains the phase value of each position on the sampling line 120 and calculates the average value of all the phase values as an on-cell phase value (step S7). The phase change amount calculation unit 244 calculates the difference between the on-cell phase value obtained in step S7 and the background value obtained in step S2 and sets this difference as a phase change amount (step S8). The background value is thus subtracted in order to reduce the influence of variations in the light emission luminance of the light source unit 10 during observation, variations in sensitivity of the image sensor 11, changes in the state of a culture medium in the culture plate 12, or the like.

Next, the phase change amount determination unit 245 determines whether or not the phase change amount obtained in step S8 is a first threshold (here, 0.08 $\pi$[rad]) or smaller (step S9) and judges that the cell in the target cell area is an undifferentiated cell (step S11). When the phase change amount is the first threshold or more, it is determined whether or not the phase change amount is a second threshold (here, 0.12 $\pi$[rad]) or more (step S10). When the phase change amount is the second threshold or more, it is judged that the cell in the target cell area is an undifferentiation deviant cell (step S12). On the other hand, when the phase change amount is less than the second threshold, that is, when the phase change amount is in the range between the first threshold and the second threshold, a definite judgment is difficult to make, so that whether or not the cell is undifferentiated is judged to be indeterminate (step S13).

By performing the processing in steps S3 to S13 for each of the cell areas extracted from one phase image, the cell in the cell area is determined to be any of an "undifferentiated cell", an "undifferentiation deviant cell", or "indeterminate" in whichever case the cell is the cell in the single cell or the cell colony. Then, the determination result is recorded inside the control and processing unit 2 and displayed on the display unit 4 in response to an instruction of the observer from the input unit 3, for example.

Here, the reason for setting the sampling line for obtaining the intracellular phase value as described with reference to FIGS. 6A and 6B will be described.

In the cell analysis system of the present embodiment, an in-line holographic microscope is used as the microscopic observation unit 1. As shown in FIG. 1, in the in-line holographic microscope, the reference light 14 and the object light 15 travel substantially coaxially to reach the image sensor 11. When the cell 13 to be observed is large, that is, when the cell 13 is a cell colony, a hologram corresponding to the vicinity of the periphery of the cell 13 is a hologram formed by the interference between reference light and object light which have passed through the portion in the culture plate 12 where no cell is present. On the other hand, a hologram corresponding to the vicinity of the central portion of the cell 13 is a hologram formed by the interference between object light and reference light that partially includes light passing through the portion where the cell is present. That is, in this case, the reference light is not ideal reference light. Therefore, when the cell 13 to be observed is large, the correct phase value can be obtained near the contour line of the cell according to the measurement principle of the in-line holographic microscope, but the phase value tends to be lower in the central portion of the cell than that near the contour line.

Figure 7A:
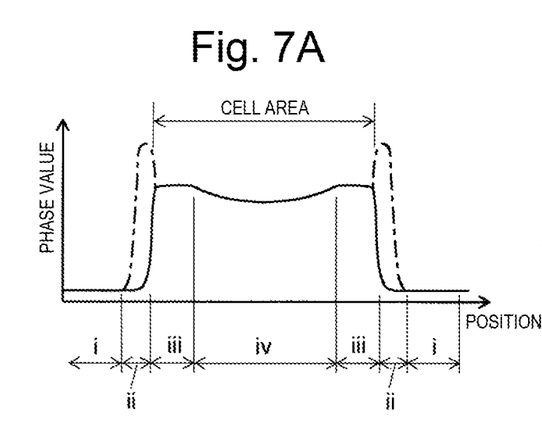
Figure 7B:
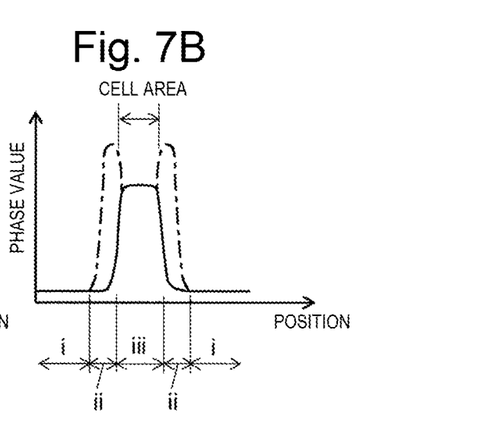

FIGS. 7A and 7B are schematic diagrams showing the schematic relationship between the position in the cross-sectional direction in the cell and the phase value, where FIG. 7A is the case of the cell colony, and FIG. 7B is the case of the single cell.

In FIGS. 7A and 7B, [i] is an area where no cell is present, that is, the background area. Further, an area [ii] in which the phase value is significantly high appears around the cell area due to halation or the like. As shown in FIG. 7B, when the cell to be observed is small (generally, the cell is a single cell), the phenomenon that the above reference light is not ideal does not occur (or its influence is small), so that the phase value is almost constant throughout the cell area. In contrast, as shown in FIG. 7A, when the cell to be observed is large (generally, the cell is a cell colony), due to above phenomenon, the phase value is almost constant in a predetermined area [iii] inside the contour line (outer edge) of the cell area, but the phase value is lower in an area [iv] which is further inside the area [iii], that is close to the central portion, than the phase value in the area [iii]. It is assumed that the amount of decrease in phase value in the area [iv] depends on the device configuration, the size of the cell, and the like, whereby the area [iv] is not appropriate to obtain a correct phase value, and the measurement needs to be performed in the area [iii].

According to the experimental study of the present inventors, the width of the area [iii] is about more than 10 µm to 20 µm, though depending on the size of the cell, and it is considered that the correct phase value in the area [iii] can be certainly obtained when measured at a position 10 µm spaced inside from the cell contour. For these reasons, in the cell analysis system of the present embodiment, the sampling line for determining the intracellular phase value has been set as described above.

Further, in the cell analysis system of the present embodiment, as described above, the determination of the undifferentiated cell and the undifferentiation deviant cell has been performed by comparing the phase change amount with two thresholds which are the first and second two thresholds. This is because it has been experimentally confirmed that there is a significant difference in optical thickness between the undifferentiated cell and the undifferentiation deviant cell, that is, there is a statistically significant difference.

Figure 8A:
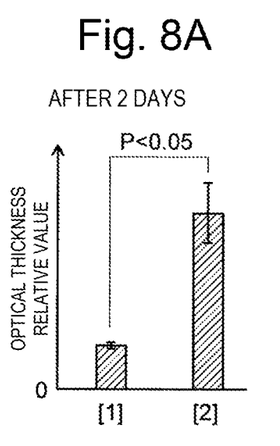
FIGS. 8A, 8B and 8C show the measurement results of the optical thicknesses of an undifferentiated cell and an undifferentiation deviant cell.
Figure 8B:
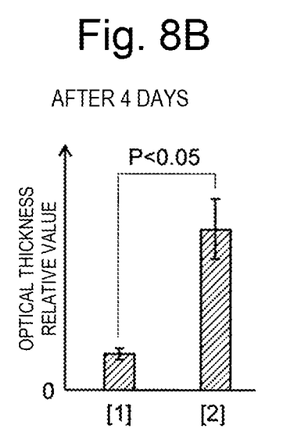
Figure 8C:
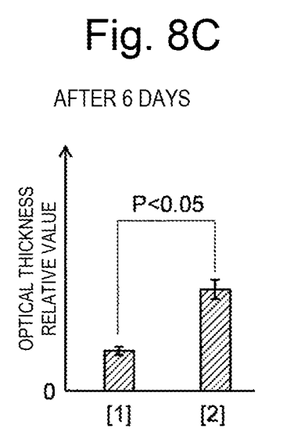

FIGS. 8A, 8B and 8C show the results of measuring the optical thicknesses of an undifferentiated cell (undifferentiated iPS cell colony) and an undifferentiation deviant cell, where [1] is the undifferentiated cell and [2] is the undifferentiation deviant cell, and FIG. 8A, 8B, and 8C are the results two days, four days, and six days after the start of culture, respectively. When a value P of the hypothesis test for the hypothesis that there is no significant difference in optical thickness between undifferentiated cell and undifferentiation deviant cell was calculated, the value P was less than 0.05 in all time periods, and it has been confirmed that there was a significant difference in optical thickness. Since the phase change amount of the cell described above reflects the optical thickness of the cell, it can be found that the undifferentiated cell and undifferentiation deviant cell can be correctly discriminated based on the phase change amount.

In the above description, various values such as 0.95 $\pi$[rad], 0.08 $\pi$[rad], 0.12 $\pi$[rad], and 10 µm are values experimentally obtained by the present inventors and are merely examples. It is easily considered that more appropriate values can be selected in accordance with the device configuration and the type of pluripotent stem cell to be observed.

Further, in the configuration of the embodiment shown in FIG. 1, all processing has been performed in the control and processing unit 2, but in general, the calculation of phase information based on hologram data and the imaging of the calculation result require an enormous quantity of calculation. For this reason, with a personal computer usually used, it takes a lot of time for calculation and efficient analysis work is difficult. It is thus preferable to use a personal computer connected to the microscopic observation unit 1 as a terminal device and use a computer system in which this terminal device and a server that is a high-performance computer are connected via a communication network such as the Internet or an intranet. In this case, complex processing such as calculation of phase information and creation of a phase image based on hologram data may be performed on the server side, the terminal device may receive the image data created by the complex processing, and the processing on the phase image formed based on the image data, that is, the processing performed by the undifferentiation/deviation-from-undifferentiation discrimination unit 24, may be performed on the terminal device side. In such a configuration, the functional blocks of the control and processing unit 2 shown in FIG. 1 are separated into the terminal device side and the server side. As thus described, the functions of the control and processing unit 2 may be shared by a plurality of computers.

Further, in the cell analysis system of the above embodiment, the in-line holographic microscope has been used as the microscopic observation unit 1, but this can naturally be replaced with another type of holographic microscope such as an off-axis type or a phase shift type so long as another type is a microscope with which a hologram can be obtained.

Furthermore, the above embodiment and the above various modifications are merely examples of the present invention, and it is apparent that, even when modification, correction, and addition are further made as appropriate in the range of the gist of the present invention, those are included in the scope of claims of the present application.

REFERENCE SIGNS LIST

1 . . . Microscopic Observation Unit
10 . . . Light Source
11 . . . Image Sensor
12 . . . Culture Plate
13 . . . Cell
14 . . . Reference Light
15 . . . Object Light
2 . . . Control and Processing Unit
20 . . . Imaging Control Unit
21 . . . Data Storage Unit
22 . . . Phase Information Calculation Unit
23 . . . Image Creation Unit
24 . . . Undifferentiation/Deviation-From-Undifferentiation Discrimination Unit
241 . . . Cell Area Extraction Unit
242 . . . Background Value Acquisition Unit
243 . . . Intracellular Phase Value Acquisition Unit
244 . . . Phase Change Amount Calculation Unit
245 . . . Phase Change Amount Determination Unit
3 . . . Input Unit
4 . . . Display Unit
100 . . . Phase Image
110 . . . Cell Area
120 . . . Sampling Line

The invention claimed is:

1. A cell analysis method using a holographic microscope, the method comprising:
 a) a cell area extraction step of extracting a cell area in which at least one cell to be analyzed is present in a phase image of an area including the cell area, the phase image being obtained from a hologram with a holographic microscope;
 b) a background value acquisition step of calculating a background value based on phase values at a plurality of positions in the area excluding the cell area in the phase image;
 c) an intracellular phase value acquisition step of obtaining an intracellular phase value based on phase values at a plurality of positions in a measurement target range between a contour line of the at least one cell in the cell area and a virtual line spaced a predetermined distance inward from the contour line; and
 d) a cell state determination step of determining whether the at least one cell to be analyzed is in an undifferentiated state or an undifferentiation deviant state based on a difference between the phase value obtained in the intracellular phase value acquisition step and the background value.

2. The cell analysis method according to claim 1, wherein when the at least one cell to be analyzed is a single cell, the predetermined distance is a value that is set in advance so that the whole cell is included in the measurement target range.

3. The cell analysis method according to claim 1, wherein in the cell state determination step, it is judged that the at least one cell to be analyzed is in the undifferentiation deviant state when the difference is equal to or greater than a first threshold value, and it is judged that the at least one cell to be analyzed is in the undifferentiated state when the difference is equal to or smaller than a second threshold value that is smaller than the first threshold value.

4. The cell analysis method according to claim 1, wherein in the intracellular phase value acquisition step, a sampling line is set along a contour line of the at least one cell within the measurement target range, and an average value of a plurality of phase values obtained on the sampling line is calculated and taken as the intracellular phase value.

5. The cell analysis method according to claim 1, wherein the holographic microscope is an in-line holographic microscope, and
 the measurement target range is a range in the cell area indicating a phase value higher than that in an area surrounded by the measurement target range.

6. A cell analysis system using a holographic microscope, the system comprising:
 at least one processor configured to
 a) extract a cell area in which at least one cell to be analyzed is present in a phase image of an area including the cell area, the phase image being obtained from a hologram with a holographic microscope;
 b) calculate a background value based on phase values at a plurality of positions in the area excluding the cell area in the phase image;
 c) obtain an intracellular phase value based on phase values at a plurality of positions in a measurement target range between a contour line of the at least one cell in the cell area and a virtual line spaced a predetermined distance inward from the contour line; and
 d) determine whether the at least one cell to be analyzed is in an undifferentiated state or an undifferentiation deviant state based on a difference between the obtained phase value and the background value.

7. The cell analysis system according to claim 6, wherein when the at least one cell to be analyzed is a single cell, the predetermined distance is a value that is set in advance so that the whole cell is included in the measurement target range.

8. The cell analysis system according to claim 6, wherein
the at least one processor is further configured to judge that the at least one cell to be analyzed is in the undifferentiation deviant state when the difference is equal to or greater than a first threshold value, and judges that the at least one cell to be analyzed is in the undifferentiated state when the difference is equal to or smaller than a second threshold value that is smaller than the first threshold value.

9. The cell analysis system according to claim 6, wherein
the at least one processor is further configured to determine a sampling line along a contour line of the at least one cell within the measurement target range, calculates an average value of a plurality of phase values obtained on the sampling line, and takes the average value as the intracellular phase value.

10. The cell analysis system according to claim 6, wherein
the holographic microscope is an in-line holographic microscope, and
the measurement target range is a range in the cell area indicating a phase value higher than that in an area surrounded by the measurement target range.

\* \* \* \* \*